(12) United States Patent
Sadik et al.

(10) Patent No.: US 10,220,185 B2
(45) Date of Patent: Mar. 5, 2019

(54) DISPOSABLE CATHETER WITH SELECTIVELY DEGRADABLE INNER CORE

(71) Applicant: Hollister Incorporated, Libertyville, IL (US)

(72) Inventors: Adel M. Sadik, Fox River Grove, IL (US); Joel D. Shutt, Gurnee, IL (US); Seamus T. Kavanagh, Libertyville, IL (US); Moh-Ching Oliver Chang, Lake In The Hills, IL (US); Bettakeri S. Udayakumar, Darien, IL (US); Eric J. Beckemeyer, Greyslake, IL (US)

(73) Assignee: Hollister Incorporated, Libertyville, IL (US)

( * ) Notice: Subject to any disclaimer, the term of this patent is extended or adjusted under 35 U.S.C. 154(b) by 722 days.

(21) Appl. No.: 14/441,057

(22) PCT Filed: Mar. 15, 2013

(86) PCT No.: PCT/US2013/031873
§ 371 (c)(1),
(2) Date: May 6, 2015

(87) PCT Pub. No.: WO2014/077886
PCT Pub. Date: May 22, 2014

(65) Prior Publication Data
US 2015/0297862 A1    Oct. 22, 2015

Related U.S. Application Data

(60) Provisional application No. 61/726,098, filed on Nov. 14, 2012.

(51) Int. Cl.
*A61M 25/00*    (2006.01)
*A61L 29/04*    (2006.01)
*A61L 29/14*    (2006.01)

(52) U.S. Cl.
CPC ....... *A61M 25/0043* (2013.01); *A61L 29/041* (2013.01); *A61L 29/146* (2013.01);
(Continued)

(58) Field of Classification Search
CPC .......... A61M 25/0043; A61M 25/0009; A61M 25/0054; A61M 2205/0065;
(Continued)

(56) References Cited

U.S. PATENT DOCUMENTS 3,583,391 A    6/1971    Cox et al.
3,621,848 A    11/1971   Magovern
(Continued)

FOREIGN PATENT DOCUMENTS

CN    2240371       11/1996
CN    101300036 A   11/2008
(Continued)

OTHER PUBLICATIONS

Notification of Transmittal of the International Search Report and the Written Opinion of the ISA for PCT/US2013/031873 dated Mar. 15, 2013 (Mar. 15, 2013).
(Continued)

*Primary Examiner* — Philip R Wiest
(74) *Attorney, Agent, or Firm* — Cook Alex Ltd.

(57) ABSTRACT

A flushable catheter having an outer wall defining an inner conduit and an inner core member positioned within the inner conduit. The inner core being made from flushable materials, which are preferably degradable water soluble materials such that the inner core degrades as urine or water pass through the inner conduit defined by the outer wall.

20 Claims, 4 Drawing Sheets

(52) U.S. Cl.
CPC ....... *A61L 29/148* (2013.01); *A61M 25/0009* (2013.01); *A61M 25/0054* (2013.01); *A61M 2025/0065* (2013.01); *A61M 2210/1096* (2013.01)

(58) Field of Classification Search
CPC .......... A61M 2210/1096; A61L 29/041; A61L 29/146; A61L 29/148
USPC ....................................................... 604/544
See application file for complete search history.

(56) References Cited

U.S. PATENT DOCUMENTS

| | | | |
|---|---|---|---|
| 3,702,610 A | 11/1972 | Sheppard et al. |
| 3,861,396 A | 1/1975 | Vaillancourt et al. |
| 3,894,540 A | 7/1975 | Bonner, Jr. |
| 4,062,363 A | 12/1977 | Bonner, Jr. |
| 4,100,309 A | 7/1978 | Micklus et al. |
| 4,227,533 A | 10/1980 | Godfrey |
| 4,413,986 A | 11/1983 | Jacobs |
| 4,465,481 A | 8/1984 | Blake |
| 4,610,671 A | 9/1986 | Luther |
| 4,668,221 A | 5/1987 | Luther |
| 4,762,738 A | 8/1988 | Keyes et al. |
| 4,769,005 A | 9/1988 | Ginsburg et al. |
| 4,772,279 A | 9/1988 | Brooks et al. |
| 4,790,817 A | 12/1988 | Luther |
| 4,790,831 A | 12/1988 | Skribiski |
| 4,795,439 A | 1/1989 | Guest |
| 4,840,622 A | 6/1989 | Hardy |
| 4,883,699 A | 11/1989 | Aniuk et al. |
| 4,906,238 A | 3/1990 | Greenfeld et al. |
| 4,952,359 A | 8/1990 | Wells |
| 4,954,129 A | 9/1990 | Giuliani et al. |
| 4,994,047 A | 2/1991 | Walker et al. |
| 5,002,526 A | 3/1991 | Herring |
| 5,009,648 A | 4/1991 | Aronoff et al. |
| 5,089,535 A | 2/1992 | Malwitz et al. |
| 5,098,535 A | 3/1992 | Nakakoshi et al. |
| 5,102,401 A | 4/1992 | Lambert et al. |
| 5,195,962 A | 3/1993 | Martin et al. |
| 5,270,086 A | 12/1993 | Hamlin |
| 5,439,454 A | 8/1995 | Lo et al. |
| 5,468,526 A | 11/1995 | Allen et al. |
| 5,472,417 A | 12/1995 | Martin et al. |
| 5,569,219 A | 10/1996 | Hakki et al. |
| 5,601,538 A | 2/1997 | Deem |
| 5,616,126 A | 4/1997 | Malekmehr et al. |
| 5,688,459 A | 11/1997 | Mao et al. |
| 5,776,611 A | 7/1998 | Elton et al. |
| 5,792,114 A | 8/1998 | Fiore |
| 5,800,412 A | 9/1998 | Zhang et al. |
| 5,804,653 A | 9/1998 | Weng |
| 5,904,703 A | 5/1999 | Gilson |
| 5,985,394 A | 11/1999 | Mao et al. |
| 6,017,334 A | 1/2000 | Rawls |
| 6,030,369 A | 2/2000 | Engelson et al. |
| 6,063,063 A | 5/2000 | Harboe et al. |
| 6,066,120 A | 5/2000 | Whiteside |
| 6,071,618 A | 6/2000 | Cook, Jr. et al. |
| 6,090,075 A | 7/2000 | House |
| 6,213,990 B1 | 4/2001 | Roempke |
| 6,217,569 B1 | 4/2001 | Fiore |
| 6,447,835 B1 | 9/2002 | Wang et al. |
| 6,468,245 B2 | 10/2002 | Alexandersen |
| 6,471,684 B2 | 10/2002 | Dulak et al. |
| 6,488,659 B1 | 12/2002 | Rosenman |
| 6,585,721 B2 | 7/2003 | Fiore |
| 6,627,586 B1 | 9/2003 | Brooks et al. |
| 6,656,146 B1 | 12/2003 | Clayman et al. |
| 6,664,333 B2 | 12/2003 | Wang et al. |
| 6,713,140 B2 | 3/2004 | McCormack et al. |
| 6,726,654 B2 | 4/2004 | Rosenman |
| 6,942,635 B2 | 9/2005 | Rosenblatt et al. |
| 6,960,224 B2 | 11/2005 | Marino et al. |
| 6,976,973 B1 | 12/2005 | Ruddell et al. |
| 7,037,295 B2 | 5/2006 | Tiernan et al. |
| 7,128,862 B2 | 10/2006 | Wang |
| 7,156,824 B2 | 1/2007 | Rosenman |
| 7,182,906 B2 | 2/2007 | Chen |
| 7,402,620 B2 | 7/2008 | McGhee |
| 7,553,923 B2 | 6/2009 | Williams |
| 7,601,158 B2 | 10/2009 | Ouse |
| 7,641,757 B2 | 1/2010 | Kampa et al. |
| 7,662,146 B2 | 2/2010 | House |
| 7,731,740 B2 | 6/2010 | LaFont et al. |
| 7,789,873 B2 | 9/2010 | Kubalak et al. |
| 7,815,628 B2 | 10/2010 | Devens, Jr. |
| 7,820,284 B2 | 10/2010 | Terry |
| 7,824,517 B2 | 11/2010 | Kampa et al. |
| 7,833,280 B2 | 11/2010 | Stack et al. |
| 7,947,031 B2 | 5/2011 | DiMatteo et al. |
| 8,143,368 B2 | 3/2012 | Domb et al. |
| 8,168,249 B2 | 5/2012 | Utas et al. |
| 8,187,254 B2 | 5/2012 | Hissink |
| 8,388,583 B2 | 3/2013 | Stout |
| 8,388,585 B2 | 3/2013 | Tomes |
| 8,469,928 B2 | 6/2013 | Stout |
| 8,518,019 B2 | 8/2013 | Green |
| 8,569,402 B2 | 10/2013 | Henderson et al. |
| 2002/0016574 A1 | 2/2002 | Wang et al. |
| 2003/0165647 A1 | 9/2003 | Kaneko et al. |
| 2003/0187368 A1 | 10/2003 | Sata et al. |
| 2003/0228434 A1 | 12/2003 | Bailey et al. |
| 2004/0122382 A1 | 6/2004 | Johnson et al. |
| 2004/0210180 A1 | 10/2004 | Altman |
| 2004/0220550 A1 | 11/2004 | Schryver |
| 2004/0230177 A1 | 11/2004 | DiMatteo et al. |
| 2004/0232589 A1 | 11/2004 | Kawabata et al. |
| 2005/0049577 A1 | 3/2005 | Snell et al. |
| 2005/0109648 A1 | 5/2005 | Kerzman et al. |
| 2005/0131386 A1 | 6/2005 | Freeman et al. |
| 2005/0163844 A1 | 7/2005 | Ashton |
| 2005/0197627 A1 | 9/2005 | Huang et al. |
| 2005/0218154 A1 | 10/2005 | Selsby |
| 2005/0277862 A1 | 12/2005 | Anand |
| 2005/0283111 A1 | 12/2005 | Maurice |
| 2006/0173422 A1 | 8/2006 | Reydel et al. |
| 2006/0240064 A9 | 10/2006 | Hunter et al. |
| 2007/0043333 A1* | 2/2007 | Kampa ................ A61L 29/085 604/523 |
| 2007/0078412 A1 | 4/2007 | McGuckin, Jr. et al. |
| 2007/0088330 A1 | 4/2007 | House |
| 2007/0203502 A1 | 8/2007 | Makker et al. |
| 2007/0225649 A1 | 9/2007 | House |
| 2008/0015527 A1 | 1/2008 | House |
| 2008/0091145 A1 | 4/2008 | House |
| 2008/0097411 A1 | 4/2008 | House |
| 2008/0118544 A1 | 5/2008 | Wang |
| 2008/0147049 A1 | 6/2008 | House et al. |
| 2008/0171991 A1 | 7/2008 | Kourakis |
| 2008/0171998 A1 | 7/2008 | House |
| 2008/0172042 A1 | 7/2008 | House |
| 2008/0183262 A1 | 7/2008 | Dowling |
| 2008/0255510 A1 | 10/2008 | Wang |
| 2008/0268193 A1 | 10/2008 | Cherry et al. |
| 2008/0292776 A1 | 11/2008 | Dias et al. |
| 2008/0312550 A1 | 12/2008 | Nishtala |
| 2009/0018530 A1 | 1/2009 | Nielsen et al. |
| 2009/0036874 A1 | 2/2009 | Horowitz et al. |
| 2009/0250370 A1 | 10/2009 | Whitchurch |
| 2009/0264869 A1 | 10/2009 | Schmid et al. |
| 2010/0030197 A1 | 2/2010 | House |
| 2010/0049146 A1 | 2/2010 | Nielsen et al. |
| 2010/0098746 A1 | 4/2010 | King |
| 2010/0100116 A1 | 4/2010 | Brister et al. |
| 2010/0137743 A1 | 6/2010 | Nishtala |
| 2010/0145315 A1 | 6/2010 | House |
| 2010/0198195 A1 | 8/2010 | Nishtala et al. |
| 2010/0204682 A1 | 8/2010 | Tanghoj et al. |
| 2010/0209472 A1* | 8/2010 | Wang ................ A61K 31/337 424/423 |
| 2010/0215708 A1 | 8/2010 | Zumbuehl et al. |
| 2010/0312255 A1 | 12/2010 | Satake et al. |

(56) References Cited

U.S. PATENT DOCUMENTS

| | | |
|---|---|---|
| 2010/0323189 A1 | 12/2010 | Illsley et al. |
| 2011/0049146 A1 | 3/2011 | Illsley et al. |
| 2011/0071507 A1* | 3/2011 | Svensson ............... A61L 29/043 604/544 |
| 2011/0114520 A1 | 5/2011 | Matthison-Hansen |
| 2011/0125135 A1 | 5/2011 | Ahmed |
| 2011/0160662 A1 | 6/2011 | Stout |
| 2011/0178425 A1 | 7/2011 | Nishtala |
| 2011/0212157 A1 | 9/2011 | Edelson et al. |
| 2011/0238163 A1* | 9/2011 | Andrews ............... A61L 29/085 623/1.46 |
| 2011/0268938 A1 | 11/2011 | Schuhmann |
| 2012/0035530 A1 | 2/2012 | Wang |
| 2012/0121919 A1 | 5/2012 | Nielsen |
| 2013/0131646 A1 | 5/2013 | Gilman |
| 2013/0345681 A1 | 12/2013 | Hong |

FOREIGN PATENT DOCUMENTS

| | | |
|---|---|---|
| DE | 10 2011 119160 A1 | 5/2013 |
| EP | 0010171 A1 | 4/1980 |
| EP | 0166998 B1 | 1/1986 |
| EP | 0613672 A1 | 9/1994 |
| EP | 0628586 B1 | 12/1994 |
| EP | 0692276 A2 | 1/1996 |
| EP | 1062920 A1 | 12/2000 |
| EP | 1110561 A2 | 6/2001 |
| EP | 141567 A1 | 5/2004 |
| EP | 2026846 A1 | 2/2009 |
| EP | 2301595 A1 | 3/2011 |
| EP | 2520412 A1 | 11/2012 |
| EP | 2609956 A1 | 7/2013 |
| GB | 2083762 | 3/1982 |
| GB | 2496901 A | 5/2013 |
| JP | S-61209655 A | 9/1986 |
| JP | 01-136662 | 9/1989 |
| JP | 11151293 | 6/1999 |
| KR | 2000/065291 A | 11/2000 |
| KR | 100754057 B | 8/2007 |
| WO | WO 89/05671 A | 6/1989 |
| WO | WO 96/41653 A1 | 12/1996 |
| WO | WO 1998/058989 A1 | 12/1998 |
| WO | WO 00/30696 A1 | 6/2000 |
| WO | WO 2006/055847 A2 | 5/2006 |
| WO | WO2006/071813 A2 | 7/2006 |
| WO | WO 2007/122269 A1 | 11/2007 |
| WO | WO 2007/140320 A2 | 12/2007 |
| WO | WO 2010/043565 A1 | 4/2010 |
| WO | WO 2011/076211 A1 | 6/2011 |
| WO | WO 2012/163413 A1 | 12/2012 |
| WO | WO 2012/166967 A1 | 12/2012 |
| WO | WO 2014/193402 A1 | 12/2014 |

OTHER PUBLICATIONS

Canadian Office Action dated Apr. 11, 2016, for Application No. 2,891,121 entitled: Disposable Catheter With Selectively Degradable Inner Core.
Rachna N. Dave, Hiren M. Joshi, and Vayalam P. Benugopalan, Novel Biocatalytic Polymer-Based Antimicrobial Coatings as Potential Ureteral Biomaterial, Feb. 1, 2011, 44(2): 845-853.
Beom Soo Kim, Jeffrey S. Hrkach, Robert Langer, Biodegradable photo-crosslinked poly(ether-ester) networks for lubricious coatings, Biomaterials, vol. 21, Issue 3, Feb. 2000, pp. 259-265.
A.K. Singla, M. Chawla, Chitosan some pharmaceutical and biological aspects, an update, Journal of Pharmacy and Pharmacology, Aug. 2001, 53: 1047-1067.
FreeStyle Vie Flushable Colostomy Bag by CliniMed Ltd., retrieved from http://www.clinimed.co.uk/Stoma-Care/Products/Closed-Stoma-Bags/Freestyle-Vie-Flushable/Product-Design.aspx Jan. 1, 2014.
Australian Patent Examination Report No. 1 dated Jul. 20, 2016, for Australian Patent Application No. 2013345395.
EPO Communication pursuant to Article 94(3) EPC dated Feb. 2, 2017 for Application No. 13717598.0-1453.

* cited by examiner

DISPOSABLE CATHETER WITH SELECTIVELY DEGRADABLE INNER CORE

RELATED APPLICATION

This application is a U.S. National Stage of PCT International Patent Application No. PCT/US2013/031873, filed Mar. 15, 2013, which claims the benefit of and priority to U.S. Provisional Patent Application Ser. No. 61/726,098, filed Nov. 14, 2012, both of which are incorporated by reference herein.

FIELD OF THE INVENTION

The present disclosure generally relates to catheters made from degradable materials and, more particularly, to selectively soluble medical catheters.

BACKGROUND OF THE INVENTION

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary incontinence. With the advent of intermittent catheters, individuals with urinary system abnormalities can self-insert and self-remove intermittent catheters several times a day. Such catheters typically include a shaft made from non-biodegradable polymeric materials, such as non-biodegradable thermoplastics. One drawback associated with such non-biodegradable catheters is that they typically, while intended for disposal, are not eco-friendly in that the non-biodegradable materials of the catheter may take several years to degrade.

Individuals who use intermittent catheters to drain their bladders several times a day often use such catheters at home and in public restrooms. Intermittent catheterization involves inserting the elongated shaft of the catheter through the urethra and into the bladder. The urine in the bladder is drained from the bladder through the catheter and into a collection bag. After the bladder has been drained, the catheter is disposed of in a waste container. Oftentimes, especially in a public restroom, it is difficult to find a suitable waste container to dispose of the catheter, and if the individual has to carry the catheter some distance to a waste container, there may be some risk of leakage or spillage of bodily fluids. Additionally, the individual, especially in a public restroom, may be uncomfortable or too embarrassed with carrying a used catheter to the waste container. In such situations, the individual may attempt to dispose of the catheter by flushing it down the toilet. For anatomical reasons urinary catheters used by males are substantially longer than those used by females. An intermittent urinary catheter for an adult male can be as long as 40 cm. Flushing such catheters down the toilet can cause major plumbing problems, such as clogging. Because the catheters are non-degradable, flushing male or female urinary catheters down the toilet also raises environmental concerns.

The present disclosure provides catheters that allow for a convenient, discreet and eco-friendly way of disposing of used catheters and catheter assemblies.

SUMMARY OF INVENTION

One aspect of the present disclosure relates to a disposable catheter including a flexible elongated shaft including an outer wall surrounding an inner conduit. The catheter also includes a degradable inner core extending at least partially within the conduit wherein the inner core is degradable upon contact with fluid, such as urine or water. The outer wall is preferably formed from a polymeric material which may be a flushable, degradable and/or a biodegradable polymeric material. The degradable inner core is preferably formed from a soluble and/or biodegradable material.

Another aspect of the present disclosure relates to a selectively degradable catheter that comprises a flexible elongated shaft including a degradable outer wall surrounding an inner conduit and a degradable inner core extending at least partially within the conduit wherein the inner core degrades faster than the outer core.

In another aspect, an intermittent urinary catheter that comprises a flexible elongated shaft including a proximal insertion end portion, a distal end portion and an outer wall surrounding an inner conduit, wherein the outer wall is comprised of a first water soluble material. The catheter also comprises an inner core extending at least partially within the conduit wherein the inner core is comprised of a second water or urine soluble material which dissolves faster than the first water soluble material.

In yet another aspect, a method of using a catheter wherein the method comprises inserting an elongated catheter into a lumen of a human body. The elongated catheter having a degradable outer wall surrounding an inner conduit and a degradable inner core extending along at least a portion of the conduit. Fluid is passed fluid through the conduit of the elongated catheter wherein the fluid causes degradation of the inner core. The catheter is then removed from the lumen of the body.

In yet a further aspect, a method of making a catheter having a shaft including an outer wall surrounding an inner core. The method comprises co-extruding the outer wall and inner core. The inner core being constructed to dissolve at a faster rate than the outer wall.

These and other aspects of the present invention are set forth in the following detailed description. In that respect, it should be noted that the present invention includes a number of different aspects which may have utility alone and/or in combination with other aspects. Accordingly, the above summary is not an exhaustive identification of each such aspect that is now or may hereafter be claimed, but represents an overview of the present invention to assist in understanding the more detailed description that follows. The scope of the invention is as set forth in the claims now or hereafter filed.

BRIEF DESCRIPTION OF THE FIGURES

In the course of this description, reference will be made to the accompanying drawings, wherein.

DETAILED DESCRIPTION

Figure 1:
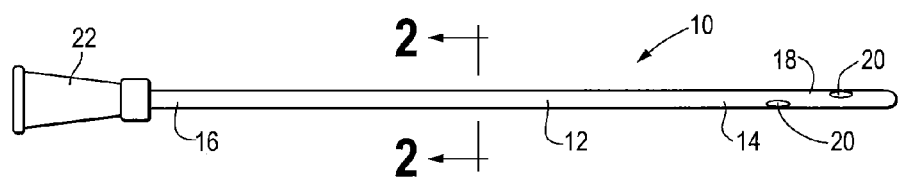
FIG. 1 is a side view of a catheter of the present disclosure.

Referring to FIG. 1, catheter 10 includes an elongated shaft 12 having a proximal insertion end portion 14 and a distal end portion 16. Proximal insertion end portion 14 includes a proximal end insertion tip 18 that is suitable for insertion into a lumen or a passageway of the body, such as the urethra. Proximal end insertion tip 18 includes draining holes or eyes 20 for the drainage of bodily fluids therethrough and into an internal conduit or lumen of shaft 12. Distal end portion 16 may include a connecting member 22, such as a funnel, for fluidly connecting catheter 10 to a collection container, such as a collection bag.

Figure 2:
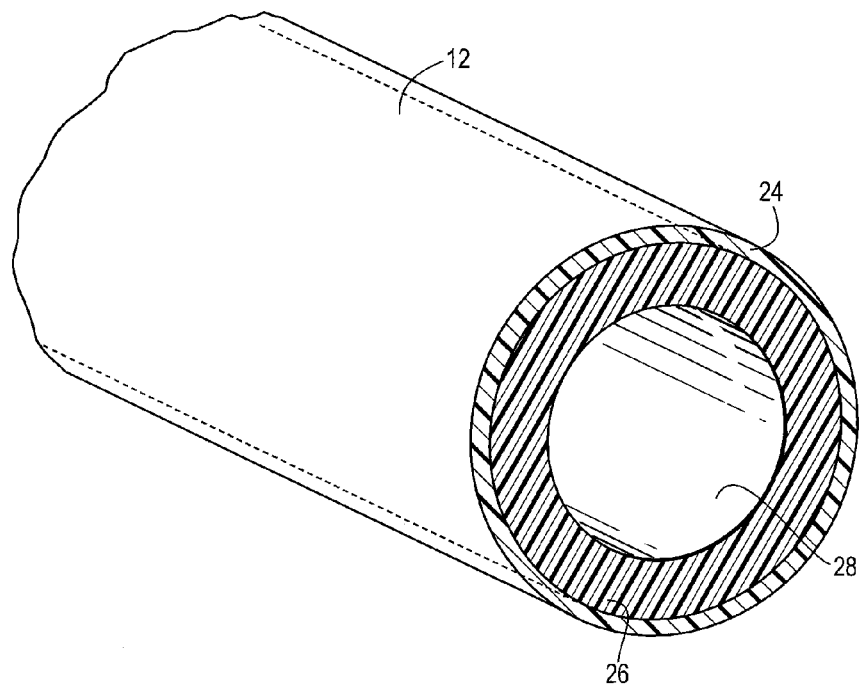
FIG. 2 is a cross-sectional perspective view of the catheter shown in FIG. 1 taken along line 2-2.

FIG. 2 is a cross-sectional view of elongated shaft 12 of catheter 10 taken along line 2-2 of FIG. 1. Elongated shaft 12 includes an outer wall or layer 24 surrounding an inner core, structure or layer 26. Outer wall 24 may circumferentially surround an internal conduit or lumen having inner core 26 located therein. Inner core 26 extends at least partially longitudinally along shaft 12 within the inner lumen defined by outer wall 24.

Inner core 26 is made from one or more flushable materials, degradable materials, such as water-soluble or urine-soluble polymer materials, and/or biodegradable materials, such as biodegradable polymers. As used herein, the term "flushable materials" refers to materials that are suitable for disposal in a toilet or sanitary sewer system. Examples of such materials are those that are included in certified flushable products that meet the National Sanitation Foundation standards for flushability or materials and products that meet INDA/EDANA Flushability Guidelines. Such "flushable materials" or catheters made from flushable materials do not necessarily need to be disposed of in a toilet, but also may be disposed in normal municipal waste systems or garbage collection systems. Additionally, as used herein, the term "degradable materials" refers to materials whose physical structure may be weakened or broken down by urine or water (e.g., materials whose structure is weakened or broken down by, for example, dissolving in urine or water); while "biodegradable materials" refer to materials that are chemically broken down by living organism or other biological means. The materials from which inner core 26 is made may have any combination of the above-described characteristics. For example, inner core 26 may be made from a flushable, biodegradable material or a flushable, soluble material.

Outer wall 24 may be made from a polymeric material. Outer wall 24 is preferably, but necessarily, made from one or more flushable materials, degradable materials, and/or biodegradable polymers.

In one embodiment, the inner core 26 extends at least partially within the inner conduit surrounded by outer wall 24 and is made from a degradable material that is degradable upon contact with urine. Preferably, the inner core 26 substantially degrades upon contact with urine and is flushed out of the inner conduit with the passage of urine therethrough.

In another embodiment, outer wall 24 and inner core 26 comprise water degradable materials, such as water soluble polymers and, in particular, relatively fast water dissolving soluble polymers. In one embodiment, the materials of the outer wall and inner core comprise cold water soluble polymers that dissolve at temperatures below about 37° C. In another embodiment, the polymer may be a water soluble polymer that dissolves at temperatures above about 37° C. The water soluble polymers may include polyvinyl alcohol, polysaccharides, polyacrylic acid, polymethacrylic acid, polyethylene glycol, poly(N-vinylpyrollidone), polyacrylamide, etc. Some exemplary water soluble polymers for outer wall 24 and inner wall 26 may include different grades of "Nichigo G-Polymer" supplied by Nippon Gohsei of Japan or Exceval AQ-4104 supplied by Kuraray of Japan.

In use, inner core 26 degrades at a faster rate than outer wall 24. For example, inner core 26 may comprise a degradable material that, during use, degrades at a faster rate than outer wall 24. In one embodiment, outer wall 24 is made of a water soluble polymer that dissolves more slowly in water than the water soluble polymer of inner core 26. In other words, inner core 26 is made from a water soluble polymer that dissolves faster in water or biological fluids than the water soluble polymer of outer wall 24. In other embodiments, inner core 26 and outer wall 24 may be comprised of the same material or different materials having substantially the same solubility, but inner core 26 may dissolve at a faster rate because of physical or structural characteristics of the inner core and/or outer wall. For example, inner core 26 may be made of less material than outer wall 24 and thus there is less material to dissolve. Alternatively, inner core 26 may include a larger surface area for contacting fluid than outer wall 24, which also could result in inner core 26 dissolving at a rate faster than outer core 24.

Figure 3:
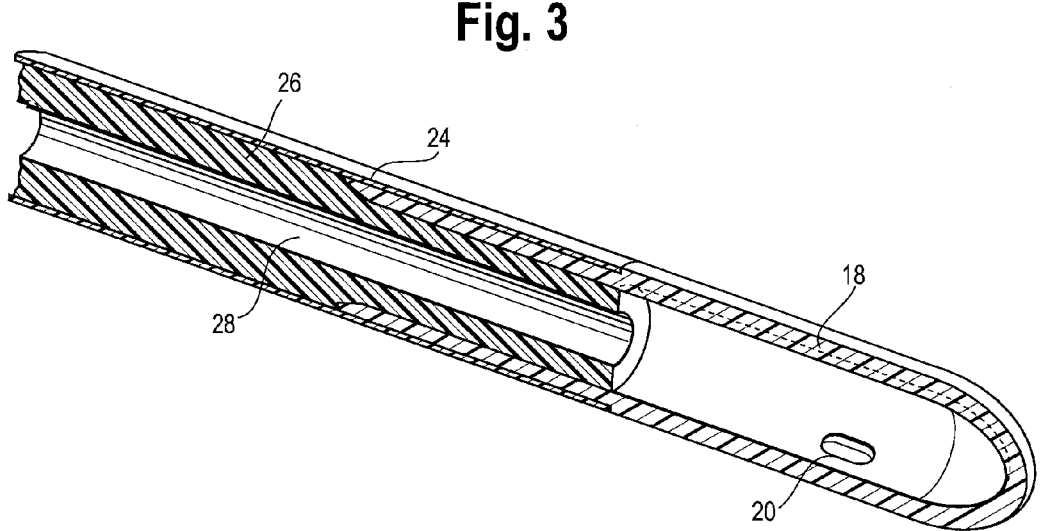
FIG. 3 is a partial cross-sectional perspective view taken along the longitudinal axis of the catheter shown in FIG. 1.

In the embodiment illustrated in FIGS. 2 and 3, inner core 26 extends radially inwardly from outer wall 24 to a fluid sub-passageway 28 defined by inner core 26. Fluid sub-passageway 28 provides a substantially unrestricted passageway for fluid flow through shaft 12. In this embodiment, inner core 26 is coaxial with outer wall 24 wherein inner core 26 defines a sub-passageway 28 that has a generally circular cross-sectional shape. In other embodiments, and as described in more detail below, the inner core may be any number of various configurations that define or at least partially define one or more fluid sub-passageways of various cross-sectional shapes, geometries and/or sizes.

The desired flexibility of shaft 12 may depend in part, upon the intended use. For example, if shaft 12 is intended to be inserted into a curved or even tortuous body lumen such as the male urethra, the shaft will have sufficient flexibility to be advanced through and bent around the curves of the tortuous path of the lumen without causing injury to the body lumen. At the same time, shaft 12 should also have sufficient rigidity or stiffness such that it can be inserted into and advanced or pushed through the tortuous lumen without unwanted bending or collapse. The balance between the desired flexibility and rigidity of shaft 12 may be achieved by varying or adjusting the amounts of the materials, incorporating different materials, their blends, degradation catalysts/triggers, thickness and configurations and/or shapes of the outer wall 24 and inner core 26.

Inner core 26 may act as a structural reinforcement member that enhances the rigidity and/or the radial incompressibility of shaft 12. For example, the amount, shape, size and type of material of inner core 26 may be configured, depending on the desired application, to increase the rigidity of shaft 12 to a desired stiffness. In one embodiment, inner core 26 provides sufficient rigidity to be able to push shaft 12 through the tortuous path in the lumen of a male urethra, but also have sufficient flexibility to bend or curve along the tortuous path of the lumen.

Inner core 26 also may reinforce outer wall 24 so as to increase the incompressibility of shaft 12 such that shaft 12 and outer wall 24 substantially retain their shape or at least do not completely collapse during use. The amount, shape, size and type of material of inner core 26 may be varied depending on the desired application and expected compressive forces to which shaft 12 may be exposed. In one example, shaft 12 is inserted through the male urethra, where it will pass through some areas of constrictions in the location of the prostrate and urethral sphincters. Such areas of constriction may produce a force that may cause shaft 12 and outer wall 24 to collapse if not for the reinforcement provided by inner core 26. In other words, inner core 26 may be configured to reinforce outer wall 24 of shaft 12 so that outer wall 24 does not completely collapse when placed under a compressive force and the fluid conduits and/or sub-passageway remain at least partially open to allow the passage of fluid therethrough.

The configuration of inner core 26 also may be varied to vary the flexibility of shaft 12 along its length. When inner core 26 extends substantially from proximal end insertion portion 14 to distal end portion 16 of elongated shaft 12, the flexibility of shaft 12 may be substantially uniform along the shaft. In other embodiments, inner core 26 may only extend and be coaxial with a portion of shaft 12. For example, inner core 26 may intermittently extend along different sections of shaft 12 to create reinforced and unreinforced areas that result in a varied flexibility along the length of shaft 12. Additionally, the configuration of inner core 26 also may effect and allow for variations in other physical properties, such as for example, mass per unit length of shaft 12, flexural modulus, and compressive strength.

Inner core 26 and the sub-passageway(s) defined thereby can be any variety of regular or irregular shapes, geometry and/or sizes. Various exemplary configurations of inner core 26 and sub-passageways are shown in FIGS. 2, 4A-4G and 5. Each configuration may provide a different amount of rigidity and reinforcement to shaft 12. Additionally, each configuration may provide a different amount of exposed surface area that will be contacted by fluid as it passes through lumen 32 and the respective sub-passageways. The amount of surface area that is contacted by fluid can have an effect on the time it takes to dissolve the inner core. Preferably the amount of material and exposed surface area, solubility of the material and shape of the inner core is optimized such that substantially all of or the majority of the inner core is dissolved by the time drainage is completed. There also may be applications wherein it is desired to optimize the above-identified features so that a certain percentage of the inner core remains after drainage is complete.

Figure 4A:
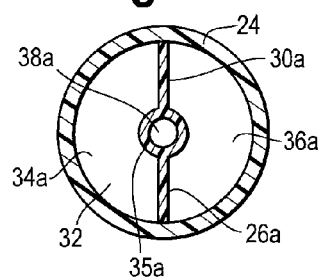
FIGS. 4A-4G are cross-sectional views of alternative configurations of the catheter shown in FIG. 1.
Figure 4B:
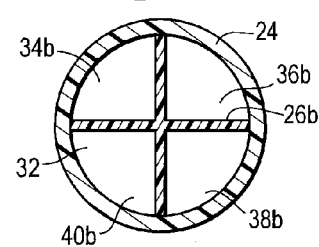
Figure 4C:
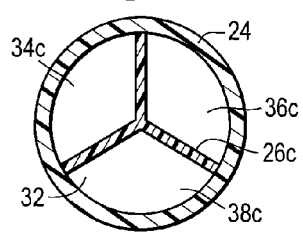

In all of the embodiments illustrated in FIGS. 4A-4G, the inner core is located within a fluid lumen conduit 32 defined by with outer wall 24. The inner core may define or partially define a single flow path or as shown in FIGS. 4A-4F a plurality of flow paths. Turning to FIG. 4A, inner core 26a includes a wall 30a that generally bifurcates fluid conduit 32 and partially defines two sub-passageways 34a and 36a. As further shown in FIG. 4A, dividing wall 30a may also include a third sub-passageway 38a preferably coaxial with inner core 24.

Figure 4D:
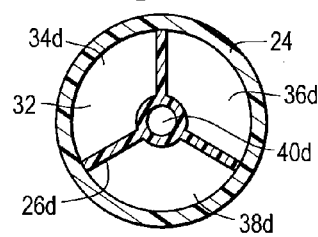
Figure 4E:
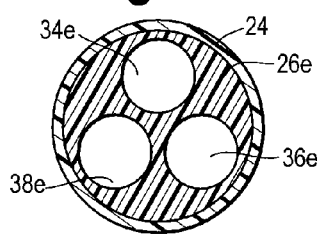
Figure 4F:
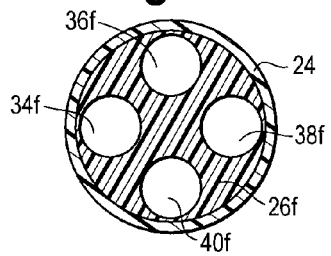
Figure 4G:
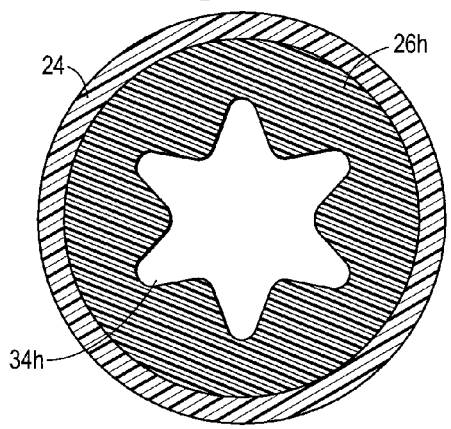

In another embodiment, the inner core may divide conduit 32 into four sub-passageways. For example, inner core 26b of FIG. 4B has a generally cross-shaped cross-section that divides conduit 32 into four sub-passageways 34b, 36b, 38b and 40b. In this embodiment, each sub-passageway has a generally triangular or pie-shaped cross-section. In yet another embodiment, the inner core trifurcates lumen 32. For example, inner core 26c of FIG. 4C has a generally peace sign shaped cross-section that divides conduit 32 into three sub-passageways 34c, 36c and 38c wherein each sub-passageway has a generally triangular or pie-shaped cross-section. Inner core 26d of FIG. 4D is similar to inner core 26c in that it has a generally peace sign shaped cross-section that divides conduit 32 into three sub-passageways 34d, 36d and 38d wherein each sub-passageway has a generally triangular or pie-shaped cross-section. Inner core 26d also includes a generally arcuate and preferably generally circular center 35d that defines a fourth sub-passageway 40d. Inner cores 26e and 26f of FIGS. 4E and 4F, respectively, substantially fill lumen 32 and define generally arcuate and preferably generally circular sub-passageways. Inner core 26e defines three sub-passageways 34e, 36e and 38e and inner core 26f defines four sub-passageways 34f, 36f, 38f and 40f. In the embodiment illustrated in FIG. 4G, inner core 26h extends inwardly from outer wall 26 and defines a generally star-shaped fluid sub-passageway 34h. As mentioned above, the fluid sub-passageway may take on any number of cross-sectional shapes, such as, polygonal and arcuate shapes, including but not limited to, square, rectangular, triangular, oval, crescent, semi-circular, etc. Additionally, the cross-sectional shape and size of the sub-passageway and inner core may vary along the longitudinal length of the shaft 12.

Figure 5:
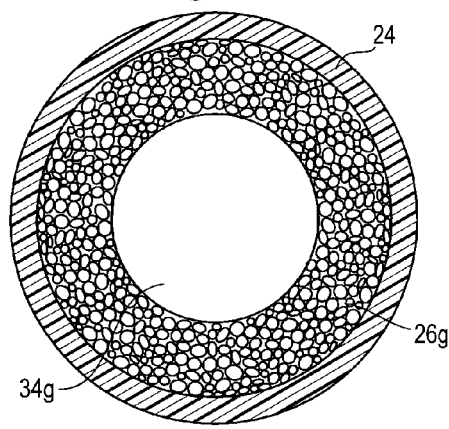
FIG. 5 is a cross-sectional view of another alternative configuration of the catheter shown in FIG. 1.

FIG. 5 illustrates another embodiment in which inner core 26g is comprised of an open-celled polymer foam that may be formed, for example, by use of a foaming agent in the manufacturing process. For instance, a chemical or physical foaming agent may be added to the polymer during an extrusion or injection molding process. In this embodiment, the open celled foam of inner core 26g extends radially inwardly from the interior surface of outer wall 24 to a fluid sub-passageway 34g defined by the inner core. In one exemplary embodiment, the thickness of outer wall 24 may be equal to or less than about 10 mils (0.254 mm) and the thickness of inner core extending radially between outer wall 24 and sub-passageway 34g may be about 40 mils (1.016 mm). Additionally, sub-passageway 34g may have a diameter of about 80 mils (2.032 mm).

In another embodiment, inner core 26g may define a plurality of sub-passageways. For example, inner core 26g may have a shape or configuration similar to those shown in 4E and 4F. In yet another embodiment, inner core 26g substantially fills the lumen defined by outer wall 24 such that there are no well-defined sub-passageways, and fluid flows through the cells of the foam (and the network formed by the cells) as it passes through the shaft of the catheter.

As discussed above, shaft 12 also includes a proximal end insertion tip 18. Referring back to FIG. 3, in this embodiment proximal end insertion tip 18 is a separate piece that is connected to shaft 12 by, for example, adhesive or molding of proximal end insertion tip 18 to shaft 12. Proximal end insertion tip 18 may be, but is not necessarily, made from a degradable material. For example, proximal end insertion tip 18 may be made from the same material as outer wall 24. In another embodiment, proximal insertion tip 18 is integral with shaft 12 and is formed, for example, by open die forming and melting of outer wall 24 of shaft 12.

The shafts of the catheters disclosed herein may be made by several different processes or a combination of several different processes. In one exemplary process, outer wall 24 and inner core 26 may co-extruded. In another process, inner core 26 may be formed by an extrusion or an injection molding process and outer wall 24 can be over-extruded or over-molded over inner core 26. In yet another process, outer wall 24 and inner core 26 each may be made by a separate extrusion or injection molding process and then inner core 26 can be slid or inserted into the inner conduit defined by the outer wall 24. During the extrusion and/or injection molding process, a slip agent, such as an amide wax (e.g., erucamide, oleamide, stearyl erucamide, etc.), ester wax (e.g., ester of montanic acids, etc.), silicone oil or the like may be added to the polymer of the outer wall to create surface lubrication on the outer surface of the outer wall. In addition to or in the alternative, a coating may be applied to the outer wall after it is formed to create a lubricated surface. Such coatings may include, for example, poly(p-xylylene), polypyrroles or the like. Surface lubrication assists with insertion and advancement of the catheter through a body lumen.

In use, proximal end insertion tip 18 of shaft 12 is inserted and advanced through a lumen of the body, such as the urethra. Proximal end insertion tip 18 and outer wall 24 are preferably made from a material that has a low coefficient of friction and/or has been sufficiently lubricated so as to assist in inserting and advancing shaft 12 through the lumen. The lubricant may be applied during the manufacturing process or separately by the user prior to insertion into the body. After shaft 12 has been advanced into a desired position, a bodily fluid, such as urine, enters through openings 20 in proximal end insertion tip 18. The bodily fluid flows through insertion tip 18 and into the sub-passageway(s) defined by inner core 26, if such sub-passageway(s) are present. In some embodiments, the sub-passageway(s) allow the bodily fluid to have a substantially unrestricted flow, so that the user may readily detect that draining of fluid has begun. The ability to detect the commencement of drainage has particular application in urinary catheters wherein commencement of drainage may be used to confirm that the catheter has reached its desired location and thus, when to terminate advancement of the catheter. This may have particular application, albeit not limited to, urinary catheters where the commencement of urine flow serves as an indication that the proximal insertion end has reached the bladder. As the bodily fluid flows through the sub-passageway(s) at least partially defined by inner core 26, the water soluble material of inner core 26 dissolves, but the slower dissolving outer wall 24 does not dissolve as quickly and outer wall 24 generally retains its structure or at least does not completely collapse. Outer wall 24 also may begin to dissolve as the bodily fluid flow through shaft 12, but preferably does not substantially dissolve during drainage of fluids. After the bodily fluid has drained, the catheter is removed. Preferably the solubility or degradation rate of outer wall 24 is such that the outer wall is still sufficiently structurally intact such that it can be substantially completely retracted or pulled out from the body lumen after the desired amount of fluid has been drained. After use, catheter 10 may then be disposed of in the toilet wherein outer wall 24 substantially dissolves in the water of the toilet, during passage through the plumbing pipes or during the domestic sewage treatment process.

Figure 6:
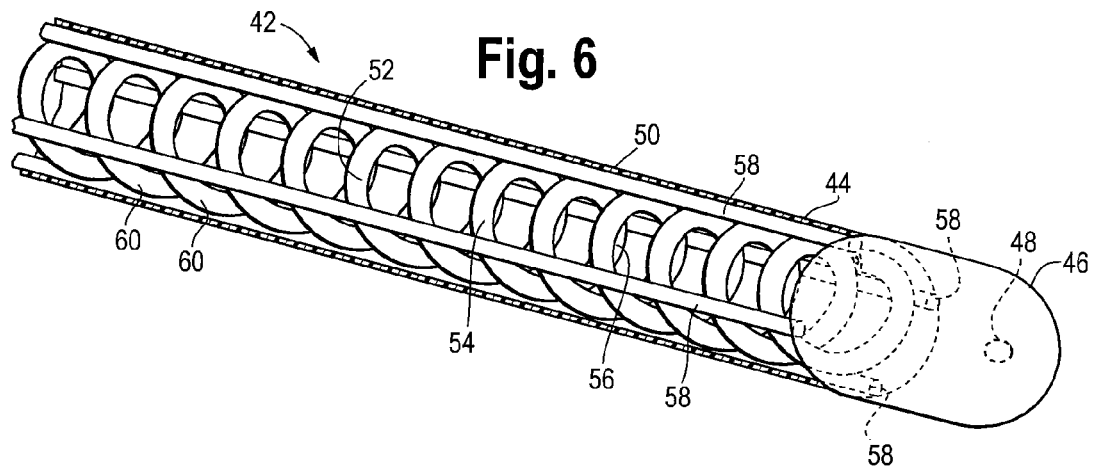
FIG. 6 is a partial perspective cross-sectional view of another embodiment of a catheter of the present disclosure.
Figure 7:
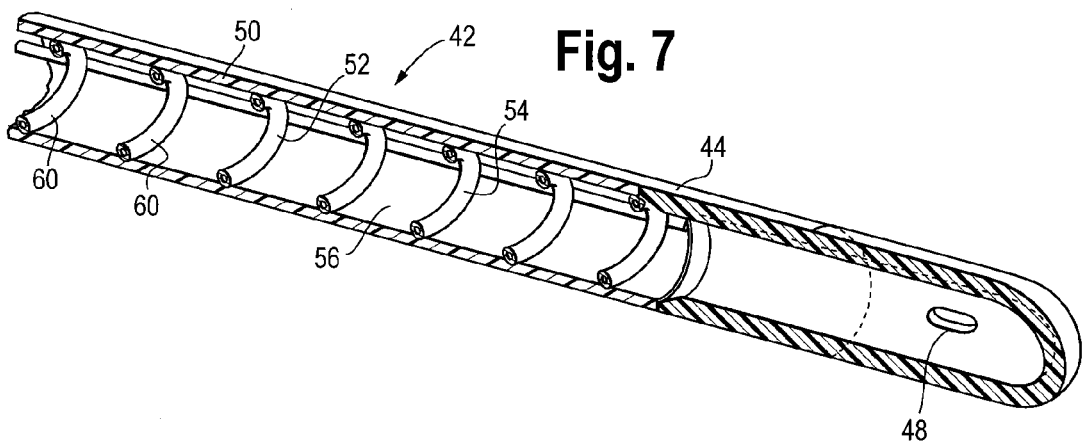
FIG. 7 is another partial perspective cross-sectional view of the catheter shown in FIG. 6.

FIGS. 6 and 7 illustrate another embodiment of a shaft 42 of a catheter of the present disclosure. Shaft 42 includes a proximal end portion 44 and a distal end portion (not shown). Proximal end portion 44 includes a proximal end insertion tip 46 that includes openings or eyes 48 in the surface of tip 46 and that allows fluid to enter the interior of the catheter. Proximal end insertion tip 46 may be formed or attached to shaft 42 by any of the processes disclosed above with respect to the other embodiments. Shaft 42 also includes an outer wall 50 and inner core 52, wherein outer wall 50 and inner core 52 are made of degradable materials such as those disclosed herein and, preferably, are made of water soluble polymers wherein the inner core 52 dissolves at a faster rate than outer wall 50. In this embodiment, inner core 52 includes a helical member 54 that extends through lumen 56 defined by outer wall 50. Inner core 52, optionally, also may include one or more stabilizing members 58 that extend longitudinally along shaft 42 and helical member 54. Stabilizing members 58 may assist in maintaining the stability of helical member 54 and/or reinforcing outer wall 50. Stabilizing members 58 also may be comprised of the same material as helical member 54 or a different material. When stabilizing members 58 are comprised of a different material, the material of stabilizing members 58 may dissolve at a different rate than outer wall 50 and helical member 54. For example, stabilizing members 58 may be made of a water soluble material that dissolves faster or slower than helical member 54 depending on the application and the structure of helical member 54. In the illustrated embodiment helical member 54 may have a substantially hollow body so that there is less material to dissolve. In other embodiments, helical member 54 may have a substantially solid body, a partially hollow body or may vary between hollow and solid along its length.

The flexibility of shaft 42 may be varied by varying the material, amount of material, pitch and configuration of helical member 54. For example, for a more rigid or stiff shaft, helical member 54 may have a tighter pitch between adjacent windings 60. Conversely, for a more flexible shaft, helical member 54 may have a wider pitch between adjacent windings 60. In one embodiment, the pitch of helical member 54 may vary along the length of shaft 42 so as to vary the flexibility of the shaft at desired locations along its length.

Figure 8:
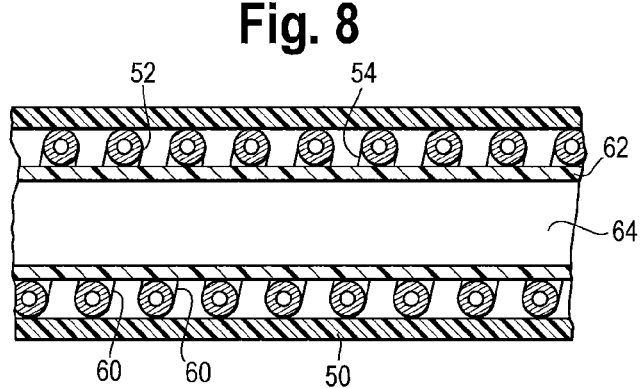
FIG. 8 is a partial cross-sectional view of another embodiment of a catheter of the present disclosure.

FIG. 8 illustrates another embodiment of a catheter of the present disclosure. This embodiment is similar to that of FIGS. 6 and 7 except that inner core 52 includes an inner layer 62 that longitudinally extends through helical member 54. Inner layer 62 may be comprised of the same material as helical member 54 or may be comprised of a different material that dissolves at a faster or slower rate than helical member 54, depending on the application. Inner layer 62 circumferentially surrounds and defines a fluid sub-passageway 64. Additionally, helical member 54 is positioned between inner layer 62 and outer wall 50, which assists in stabilizing helical member 54.

The catheter shafts of FIGS. 6-8 may be made by any of the processes disclosed herein. For example, helical member 54, stabilizing members 58, outer wall 50 and inner layer 62 (when present) may be co-extruded. Alternatively, helical member 54, stabilizing members 58 and inner layer 62 (when present) may be co-extruded or individually extruded or injection molded and formed into a sub-assembly, and then outer wall 54 may be extruded over the sub-assembly. In yet another embodiment, each of the individual components may be made separately and then assembled. For example, helical member 54, stabilizing members 58, and outer wall 50 may each be made individually by extrusion or injection molding and then helical member 54 and stabilizing members 58 may be inserted into and advanced into the inner conduit of outer wall 50.

The catheter shafts illustrated in FIGS. 6-8 operate in substantially the same manner as described above wherein shaft 42 is inserted into a body lumen to drain fluid from the body. As bodily fluids pass through shaft 42, inner core 52 (including one or more of helical member 54, stabilizing members 58 and inner layer 62) substantially dissolve(s), leaving the slower dissolving outer wall 54. After drainage is complete, shaft 42 is removed from the lumen and disposed of in the toilet, wherein outer wall 54 dissolves.

Although the present invention is described in light of the illustrated embodiments, it is understood that this for the purposes illustration and not limitation. Other applications, modifications or use of the support or distraction device may be made without departing for the scope of this invention, as set forth in the claims now or hereafter filed.

What is claimed is:

1. A disposable intermittent urinary catheter, comprising:
   a flexible elongated shaft including an outer wall surrounding an inner conduit wherein the outer wall is water degradable;
   a degradable inner core extending at least partially within the conduit, the inner core defining a structural reinforcement member that reinforces the outer wall to enhance rigidity and radial incompressibility of the elongated shaft, wherein the inner core is degradable upon contact with fluid; and
   wherein the inner core degrades at a faster rate than the outer wall.

2. The disposable intermittent catheter of claim 1 wherein the outer wall comprises a flushable material that is suitable for disposal in a toilet or sanitary sewer system.

3. The disposable intermittent catheter of claim 1 wherein the outer wall is comprised of a first degradable material and the inner core is comprised of a second degradable material.

4. The disposable intermittent catheter of claim 3 wherein the first and second degradable materials comprise water soluble materials and the second degradable material dissolves at a faster rate than the first degradable material.

5. The disposable intermittent catheter of claim 1 wherein the outer wall and/or the inner core are comprised of a polyvinyl alcohol.

6. The disposable intermittent catheter of claim 1 wherein the inner core comprises an open-celled foam.

7. The disposable intermittent catheter of claim 6 wherein the open-celled foam substantially occupies the entire conduit.

8. The disposable intermittent catheter of claim 6 wherein the open-celled foam defines a generally elongated sub-passageway therethrough for the passage of fluid.

9. The disposable intermittent catheter of claim 1 wherein the inner core at least partially defines a plurality of sub-passageways within the inner conduit configured for the passage of fluid.

10. The disposable intermittent catheter of claim 9 wherein the sub-passageways comprise generally circular and/or generally pie shaped sub-passageways.

11. The disposable intermittent catheter of claim 1 wherein the inner core bifurcates or trifurcates the inner conduit.

12. The disposable intermittent catheter of claim 1 wherein the inner core has a generally cross-shaped cross-section.

13. The disposable intermittent catheter of claim 1 wherein the inner core comprises a generally helical shape.

14. The disposable intermittent catheter of claim 13 wherein the generally helically shaped inner core is hollow.

15. The disposable intermittent catheter of claim 13 wherein the generally helically shaped inner core has a pitch that varies along the inner conduit of the elongated shaft.

16. The disposable intermittent catheter of claim 13 further including one or more stabilizing members longitudinally extending along the inner conduit of the elongated shaft.

17. The disposable intermittent catheter of claim 1 wherein the entire inner core substantially degrades during the passage of fluid through the inner conduit.

18. The disposable intermittent catheter of claim 1 wherein the inner core varies the rigidity and/or incompressibility along the elongated shaft.

19. The disposable intermittent catheter of claim 1 wherein the elongated shaft has greater flexibility after the inner core has degraded.

20. The disposable intermittent catheter of claim 1 wherein the outer wall and/or inner core are made from biodegradable materials.

* * * * *